United States Patent
Wyslucha et al.

(10) Patent No.: US 10,918,551 B2
(45) Date of Patent: Feb. 16, 2021

(54) DEVICE FOR MANUALLY UNLOCKING A HOLDING MECHANISM TO WHICH A LOAD CAN BE APPLIED

(71) Applicant: MAQUET GMBH, Rastatt (DE)

(72) Inventors: Ulrich Wyslucha, Weingarten (DE); Markus Singer, Plochingen (DE); Reinhard Gantke, Grossbettlingen (DE); Hans-Joerg Hopfengart, Aichwald (DE)

(73) Assignee: MAQUET GMBH, Rastatt (DE)

( * ) Notice: Subject to any disclaimer, the term of this patent is extended or adjusted under 35 U.S.C. 154(b) by 175 days.

(21) Appl. No.: 15/236,742

(22) Filed: Aug. 15, 2016

(65) Prior Publication Data
US 2016/0348836 A1 Dec. 1, 2016

Related U.S. Application Data

(63) Continuation-in-part of application No. 14/376,628, filed as application No. PCT/EP2013/052408 on Feb. 7, 2013.

(30) Foreign Application Priority Data

Feb. 7, 2012 (DE) .................... 10 2012 000 970

(51) Int. Cl.
*A61G 13/10* (2006.01)
*A61G 13/12* (2006.01)
(Continued)

(52) U.S. Cl.
CPC ........... *A61G 13/10* (2013.01); *A61G 13/101* (2013.01); *A61G 13/12* (2013.01); *F16H 19/04* (2013.01);
(Continued)

(58) Field of Classification Search
CPC ... F16C 11/10; A61B 19/26; A61B 2090/508; A61B 90/50; A61B 90/60; F16M 13/022;
(Continued)

(56) References Cited

U.S. PATENT DOCUMENTS 2,510,198 A * 6/1950 Tesmer .................. B23Q 1/285
248/160
3,333,808 A * 8/1967 Du Boff .................. E04G 25/04
248/200.1
(Continued)

FOREIGN PATENT DOCUMENTS

CN 101511319 A 8/2009
CN 102068360 A 5/2011
(Continued)

OTHER PUBLICATIONS

International Search Report for PCT/EP2013/052408 dated May 8, 2013.
(Continued)

*Primary Examiner* — Ingrid M Weinhold

(57) ABSTRACT

An device for manually unlocking a holding mechanism to which a load is applied is disclosed. The device has an operating element which is to be operated manually for unlocking the holding mechanism via an operating force that increases as the load increases, a conversion mechanism which includes a force transfer element coupled to the operating element, and a trigger coupled to the force transfer element. In order to unlock the holding mechanism the trigger is movable by the operating force transferred by the force transfer element to the trigger from a locked position in which the trigger is operatively decoupled from an unlocking component into an unlocked position in which the trigger is in contact with the unlocking component and unlocks said holding mechanism. The conversion mecha-
(Continued)

nism includes an elastically deformable force limiter via which the force transfer element is coupled to the trigger.

19 Claims, 13 Drawing Sheets

(51) Int. Cl.
*A61B 90/50* (2016.01)
*F16H 19/04* (2006.01)
*F16H 21/44* (2006.01)
*F16C 11/10* (2006.01)

(52) U.S. Cl.
CPC ........ *F16H 21/44* (2013.01); *A61B 2090/508* (2016.02); *A61G 13/1235* (2013.01); *F16C 11/10* (2013.01); *Y10T 74/18928* (2015.01); *Y10T 74/18976* (2015.01)

(58) Field of Classification Search
CPC .............. F16M 11/06; F16M 11/2035; F16M 2200/024; F16H 19/04; F16H 21/44; A61G 13/10; A61G 13/12; A61G 13/101; A61G 13/1235; A61G 13/1245; A61G 13/121; A61G 13/124; A61G 13/125; A61G 13/1205; Y10T 403/32024; E04G 2025/045; E04G 2025/047; E04G 2025/006; E04G 25/00; A47B 91/02
USPC ........ 248/274.1, 276.1, 280.11, 281.11, 160, 248/200.1, 188.5, 188.8; 128/846, 845, 128/878; 5/646, 623, 624, 648, 621, 647, 5/649–651; 292/47, 49; 403/109.1
See application file for complete search history.

(56) References Cited

U.S. PATENT DOCUMENTS

| | | | | |
|---|---|---|---|---|
| 3,529,797 | A * | 9/1970 | Street | F16M 11/40 248/160 |
| 3,584,822 | A * | 6/1971 | Oram | F16M 11/40 248/160 |
| 4,881,728 | A | 11/1989 | Hunter | |
| 4,898,068 | A * | 2/1990 | Neuhaus | B25B 23/1427 81/483 |
| 5,458,279 | A * | 10/1995 | Plyley | A61B 17/072 227/176.1 |
| 5,537,700 | A | 7/1996 | Way et al. | |
| 5,775,334 | A * | 7/1998 | Lamb | A61G 13/12 128/845 |
| 5,899,425 | A * | 5/1999 | Corey, Jr. | A61B 17/02 248/276.1 |
| 6,575,653 | B1 | 6/2003 | Krauter | A61G 13/101 248/276.1 |
| 6,663,563 | B1 * | 12/2003 | Sharratt | A61B 1/00149 600/227 |
| 6,698,044 | B2 * | 3/2004 | Greenfield | A61F 5/3776 248/104 |
| 6,767,153 | B1 * | 7/2004 | Holbrook | F16C 11/0604 403/115 |
| 7,136,280 | B2 * | 11/2006 | Jobs | F16M 11/14 361/679.06 |
| 7,337,808 | B2 * | 3/2008 | Shamir | E03C 1/0408 138/120 |
| 7,461,423 | B2 | 12/2008 | Rutherford | F16M 11/04 248/118 |
| 7,730,565 | B1 * | 6/2010 | Masson | A61G 13/101 5/503.1 |
| 8,056,874 | B2 * | 11/2011 | Goodwin | A61G 5/10 248/276.1 |
| 8,322,342 | B2 | 12/2012 | Soto | A61G 13/12 128/845 |
| 8,382,048 | B2 * | 2/2013 | Nesper | F16M 11/40 248/160 |
| 9,581,190 | B2 * | 2/2017 | Richman | F16B 2/02 |
| 9,782,316 | B2 * | 10/2017 | Schuerch, Jr. | A61G 13/101 |
| 10,072,793 | B2 | 9/2018 | Wyslucha et al. | |
| 2002/0014567 | A1 | 2/2002 | King | A61B 19/26 248/276.1 |
| 2004/0217239 | A1 * | 11/2004 | Chuang | A47B 96/1425 248/125.8 |
| 2008/0078031 | A1 | 4/2008 | Weinstein | A61F 5/3707 5/630 |
| 2008/0185111 | A1 * | 8/2008 | Zagone | E04G 21/24 160/379 |
| 2008/0302938 | A1 * | 12/2008 | Goodwin | A61G 5/10 248/288.51 |
| 2010/0237032 | A1 * | 9/2010 | Whitehall | A47B 57/26 211/107 |
| 2011/0242827 | A1 * | 10/2011 | Farinola | A47F 5/00 362/368 |
| 2012/0223199 | A1 | 9/2012 | Abri | A61B 19/26 248/280.11 |

FOREIGN PATENT DOCUMENTS

| | | |
|---|---|---|
| DE | 1055177 | 4/1959 |
| DE | 3101865 A1 | 1/1982 |
| DE | 10209209 B4 | 3/2006 |
| DE | 10 2006 004 126 A1 | 7/2007 |
| JP | S63176438 U | 11/1988 |
| JP | H08299394 A | 11/1996 |
| KR | 20110055468 A | 5/2011 |
| WO | 2005/007053 A2 | 1/2005 |

OTHER PUBLICATIONS

Maquet Releases Trimano 3D Assist System, Medgadget, Aug. 9, 2010, downloaded on Oct. 11, 2018 from https://www.medgadget.com/2010/08maquet_releases_trimano_3d_assist_system.html.
Accessories for Operating Tables Catalog, 11 pages.
Trimano 3D Support Arm, Product Overview, https://www.gheg.de/en/products/trimano-3d-support-arm/, printed May 7, 2019, 5 pages.
Trimano 3D Support Arm, Product Overview, https://www.maquet.com/int/products/trimano-3d-support-arm/, printed May 7, 2019, 3 pages.
Trimano Fortis, Product Overview, https://www.maquet.com/int/products/trimano-fortis/, printed May 7, 2019, 3 pages.
Trimano Fortis Support Arm, Product Overview, https://www.arthrex.com/shoulder/trimano-arm-holder/resources, 2019, printed May 7, 2019, 5 pages.

* cited by examiner

DEVICE FOR MANUALLY UNLOCKING A HOLDING MECHANISM TO WHICH A LOAD CAN BE APPLIED

CROSS REFERENCE TO RELATED APPLICATIONS

The present application is a continuation-in-part filed under 35 U.S.C. § 111(a), and claims the benefit of U.S. patent application Ser. No. 14/376,628, filed Aug. 5, 2014, which claims benefit of PCT/EP2013/052408 filed on Feb. 7, 2013, and German Patent Application No. 10201200970.8 filed Feb. 7, 2012. The disclosures of these applications are herein incorporated by reference in their entirety.

TECHNICAL FIELD

The invention relates to a device for manually unlocking a holding mechanism to which a load can be applied, comprising an operating element which is to be operated manually for unlocking the holding mechanism with an operating force becoming larger as the load increases, a conversion mechanism which includes a force transfer element coupled to the operating element, and a trigger coupled to the force transfer element, wherein in order to unlock the holding mechanism the trigger is movable by the operating force transferred by the force transfer element to the trigger from a locked position in which the trigger is operatively decoupled from the holding mechanism into an unlocked position in which the trigger is operatively coupled to the holding mechanism in order to unlock said holding mechanism.

BACKGROUND

In medical technology a mechanical assistance system is used, e.g. for supporting the arm in operations at the shoulder or at the upper arm of a patient. This assistance system is substantially formed by a holding arm. If the weight of a supported patient is relatively large, the operator has to exert a correspondingly large counteracting force after unlocking the holding arm to stabilize the holding arm. As the unlocking of the holding arm occurs promptly, the operator has to react quickly, which renders handling of the holding arm difficult. It often occurs in practice that the operator is surprised that the holding arm suddenly loses its stability during an unlocking procedure and bags downwards. This renders handling of the holding arm difficult.

SUMMARY OF THE DISCLOSURE

The present disclosure is directed to a manually operable unlocking device determined for a holding mechanism of the above-mentioned type further such that the handling thereof becomes easier and safer than has been the case so far.

The conversion mechanism may include an elastically deformable force limiter via which the force transfer element is coupled to the trigger and which prevents due to its elastic deformation the transfer of the operating force to the trigger, if the operating force exceeds a predetermined force.

The invention takes advantage of the fact that the operating force which is to be manually exerted on the operating part in order to unlock the holding mechanism depends on the load to be supported, in particular becomes larger as the load increases. The force to be applied in order to unlock the holding mechanism can be considered as a measure for the load which is applied to the holding mechanism. The circumstance that the operating force becomes larger with increasing load also includes an aspect to the effect that an unsuitable unlocking in case of a large load is prevented.

The invention provides an elastically deformable force limiter which may allow a transfer of the operating force manually exerted on the operating part to the trigger, if the operating force is not larger than a predetermined force. As the operating force, as explained above, is a measure for the load resting on the holding mechanism, the force limiter may prevent a transfer of the operating force to the trigger and thus unlocking of the holding mechanism to which the load is applied, if this load exceeds a predetermined value. Conversely, unlocking of the holding mechanism by operating of the operating part is possible (e.g., only possible) according to the invention, if the load is not larger than this predetermined value.

If the operator operates the operating part and in doing so realizes that in this way unlocking of the holding mechanism is not possible for him, the operator becomes aware that the load resting on the holding mechanism is larger than the predetermined value. After the operator has realized that, he can for example, while continuing to exert the operating force on the operating part, support with the same or his other hand the holding mechanism, in order to counteract the load resting on the holding mechanism and thus to unload the holding mechanism. If the holding mechanism is sufficiently unloaded in this manner, it becomes possible for the operator to unlock the holding mechanism by exerting the operating force on the operating part. Thereby it is reliably prevented that the operator is surprised by a sudden transfer of the holding mechanism from a load holding state to a load yielding state. Further, by the limitation of the effective operating force, unsuitable operation of the unlocking device and/or the parts forming the holding mechanism as a consequence of an unsuitable force application is prevented. Finally, by limiting the operating force good ergonomics of the handle operation is provided.

In at least some exemplary embodiments, the force limiter is a spring, the restoring force of which is dimensioned such that the spring maintains its original shape, if the operating force is smaller or equal to the predetermined force, and that the spring is elastically deformed, if the operating force exceeds the predetermined force. If the operating force is sufficiently small, the spring interconnected between the force transfer element and the trigger acts as a substantially rigid element, so that the operating force exerted on the operating part acts via the spring largely unweakened on the trigger and the holding mechanism is unlocked. If, however, the operating force exerted on the operating part is that large, that the operator should unload the holding mechanism before its unlocking, in order not to be surprised by the suddenly occurring instability of the holding mechanism, the spring absorbs as a consequence of its elastic deformation quasi the exerted operating force, whereby the latter does not act on the trigger anymore and the holding mechanism remains locked. Only with unloading of the holding mechanism the operating force to be exerted on the operating part becomes so small again that this does not cause an elastic deformation of the spring and the operating force is transferred to the trigger.

Preferably, the spring is a pressure spring, which is compressed between the force transfer element and the trigger, if the force exerted on the operating part is larger than the predetermined force.

In at least some exemplary embodiments, the conversion mechanism comprises a first toothing formed at the operating part and a second toothing formed at the force transfer element which meshes with the first toothing Such a transmission formed by two toothing patterns is particularly suitable to convert an operation of the operating part e.g. in a linear movement of the force transfer element and thus in a corresponding movement of the trigger coupled via the force limiter to the force transfer element (as far as the operating force does not exceed a predetermined force).

In an alternative embodiment, the conversion mechanism comprises a movable pressing surface formed at the operating part and a toggle lever with a longer first leg and a shorter second leg, wherein the longer first leg of the toggle lever is supported at one end in a first center of rotation stationary inside the unlocking device, the shorter second leg of the toggle lever is rotatably supported at one end in a second center of rotation, which is stationary relative to the movably guided force transfer element, the two legs are supported respectively at their other end in a common third center of rotation, and the pressing surface presses onto the toggle lever in the region of the third center of rotation when the operating part is manually operated. By using a toggle lever a delayed transmission of the operating force at constant operating speed can be obtained. For example, at constant operating speed (e.g., the stroke speed), with which the force transfer element is moved, decreases, while the force exerted by the force transfer element increases. Thus, the operating force exerted by the operator comes into effect with delay, so that the operator can better prepare for the coming unlocking of the holding mechanism when operating the operating part. Further, in this manner a larger force transmission becomes possible.

In at least some exemplary embodiments, the force transfer element includes a hollow cylindrical portion in which the force limiter is supported. This allows a particularly compact construction of the unlocking device. The trigger comprises for example a trigger rod which is linearly guided in the direction of its longitudinal axis. In this case, the trigger rod can be at least partially guided inside the oblong force limiter. If the force limiter is e.g. a coil spring, in this embodiment a part of the trigger rod extends into the interior of the coil spring. This also provides for a compact construction of the unlocking device.

In at least some exemplary embodiments, an end stop is provided, which limits the elastic deformation of the force limiter. If the force limiter is for example a compression spring, the end stop provides for the compression spring being only compressed so tightly that the spring deflection caused thereby is still within an operating region determined by a pre-defined spring-load deflection curve. The spring can fulfil its function, e.g. either allowing or preventing the transfer of the operating force exerted on the operating part, depending on the size of said force, to the trigger reliably for a long period of time.

The above-mentioned end stop is for example an end stop surface which abuts the force transfer element. In this embodiment, the end stop limits the lifting of the force transfer element. It is however also possible to assign the end stop for example to the operating part to restrict the operating path thereof.

According to a further aspect of the invention a holding mechanism to which a load can be applied is provided which comprises an unlocking device of the above-described type.

BRIEF DESCRIPTION OF THE DRAWINGS

The invention will be explained be following on the basis of the Figures, wherein.

DETAILED DESCRIPTION AND INDUSTRIAL APPLICABILITY

Figure 1:
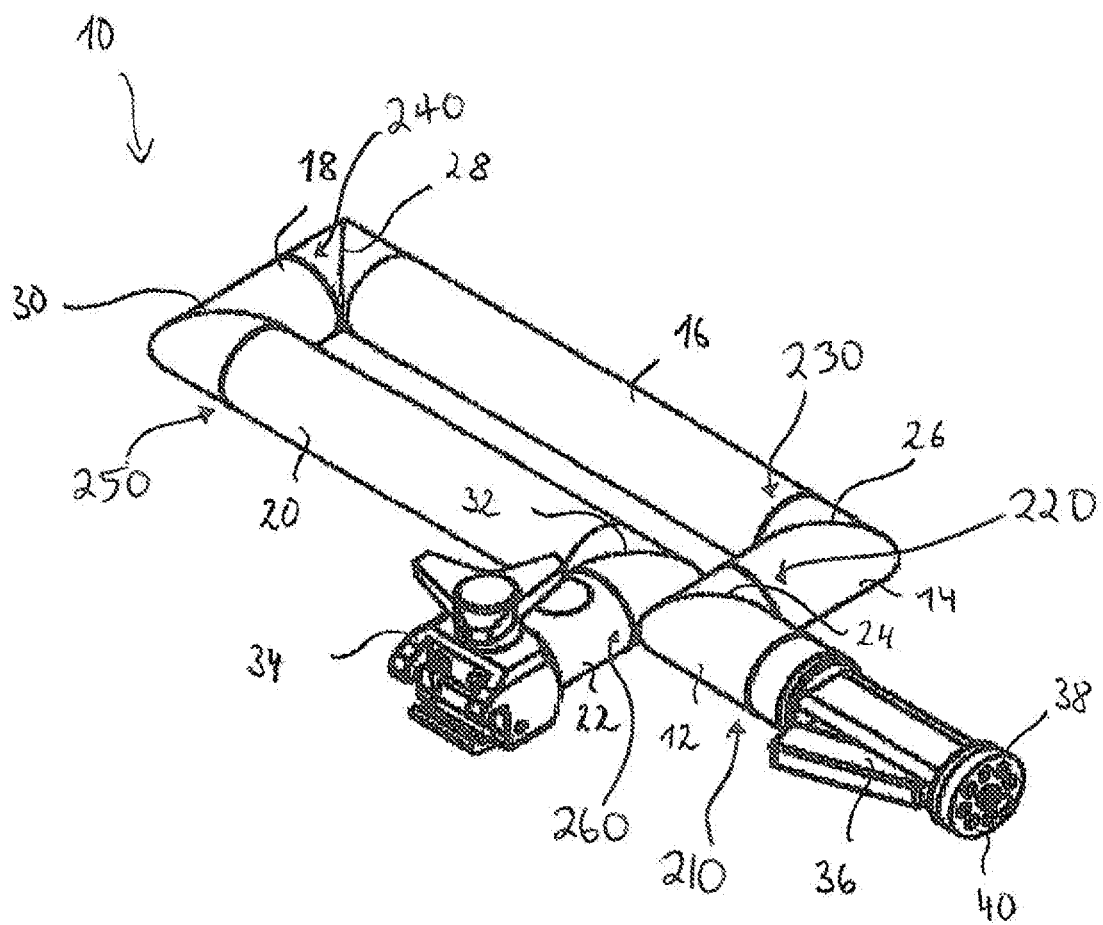
FIG. 1 shows an exemplary holding arm for supporting a patient's arm according to at least some exemplary embodiments of the present disclosure.

The exemplary holding arm 10 illustrated in FIG. 1 may include a plurality of rigid holding members 12, 14, 16, 18, 20 and 22, which are coupled together via respective rotational joints 210, 220, 230, 240, 250, and 260 and fittings (e.g., rigid fittings) 24, 26, 28, 30 and 32. At one end of the holding arm 10 a fixing device 34 is arranged which serves to attach the holding arm 10 at a sliding rail of an operating table. At the other end of the holding arm 10 a handle 36 is positioned which can be manually operated by the operator to unlock the holding arm 10 in the manner described below. At the handle 36 a holder 40 provided with a plurality of latch openings 38 is attached at which a not shown support, e.g. for supporting the patient's arm, can be attached.

The handle 36 may serve to unlock the holding arm 10, for example joints 210, 220, 230, 240, 250, and 260 coupling the individual holding members 12 to 22 together. For this, the handle 36 includes a mechanical trigger which upon compressing the handle 36 operates an unlocking rod system guided through the holding arm 10. In doing so, the operating force exerted on the handle 36 is transferred via a conversion mechanism, which is positioned inside the handle 36, to the trigger. If the trigger due to the operation of the handle 36 acts on the rod system, the latter ensures that the individual joints 210, 220, 230, 240, 250, and 260 are unlocked. Each of the joints 210, 220, 230, 240, 250, and 260 is formed such that it allows in the unlocked state a relative movement of the two holding members which are coupled to each other by said joint.

If substantially no operating force is exerted on the handle 36, the holding members 12 to 22 of the holding arm 10 may be rigidly coupled to each other via the joints 210, 220, 230, 240, 250, and 260. In this state, the holding arm 10 forms a rigid unit which is suited to support the patient's arm in a stable position. If the position of the patient's arm in the space shall be changed, the operator compresses the handle 36 causing the unlocking mechanism to be operated via the mechanical trigger. By operating the handle 36 the holding members 12 to 22 coupled to each other via the joints 210, 220, 230, 240, 250, and 260 become thus movable relative to each other, so that the operator can align the holding arm 10 as desired. If the operator subsequently releases the handle 36 again, the joints 210, 220, 230, 240, 250, and 260 are locked again and the holding arm 10 is fixed again in its changed alignment.

The operating force which the operator may exert on the handle 36 in order to unlock the holding arm 10 depends on the load which is applied to the holding arm 10. This load is composed of the proper weight of the holding arm 10 and the weight of the supported patient's arm. The heavier the patient's arm is, the larger the operating force consequently may be, which the operator has to exert on the handle 36 in order to unlock the holding arm 10.

If the operator operates the handle 36 with a sufficiently large operating force, the holding arm 10 is (e.g., promptly) unlocked. The holding arm 10 may (e.g., instantly) yield under the load, e.g. substantially the weight of the patient's arm. This yielding of the holding arm 10 is less problematic as far as the weight supported on the holding arm 10 is relatively low. In this case, the operator can counteract a sudden bagging of the holding arm 10 by exerting with his hand holding the handle 36 a counteracting force opposite to the weight of the patient's arm, e.g. he generally pushes the handle 36 a little upwards since the load acts downwards.

Figure 2:
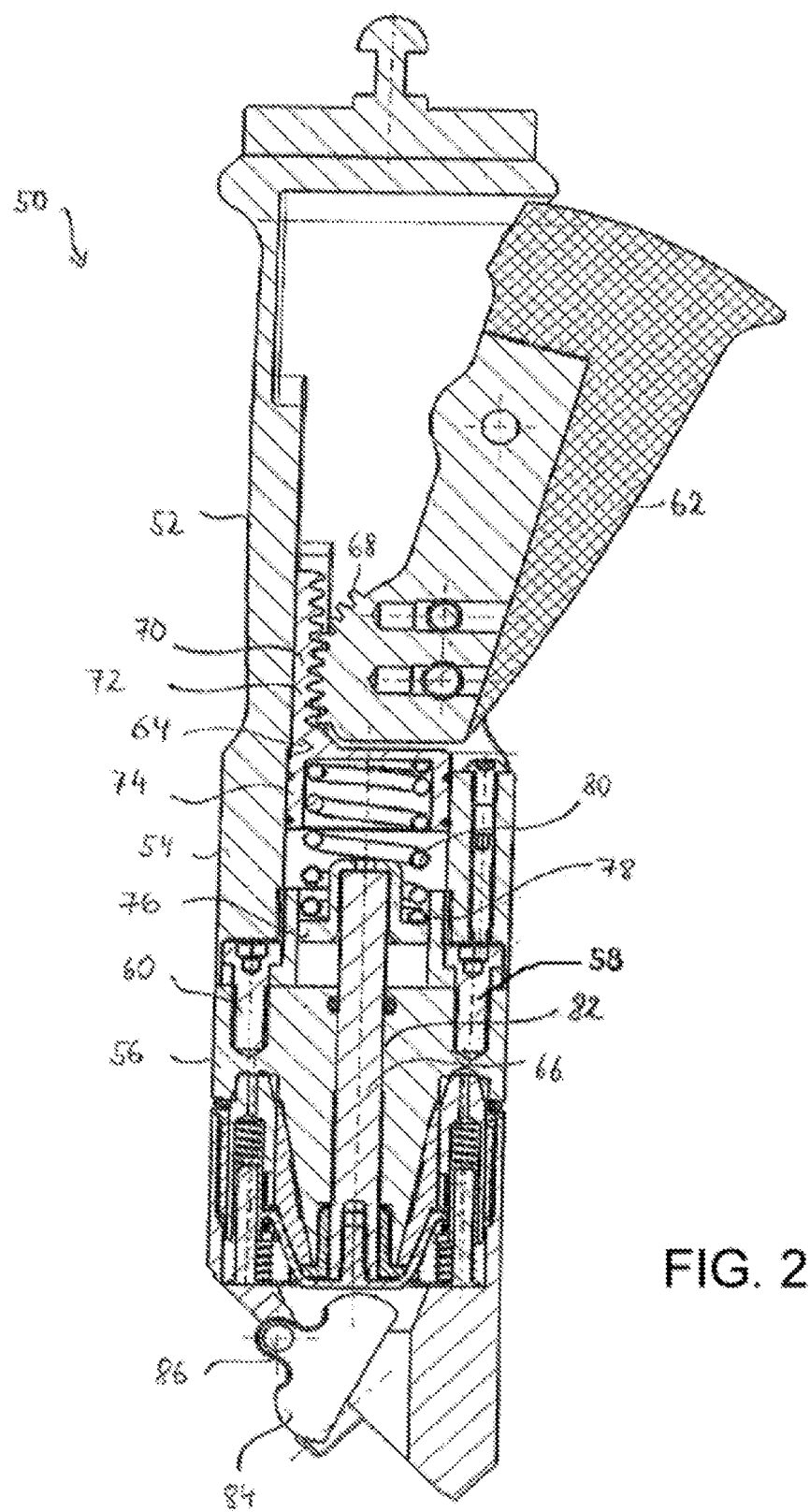
FIG. 2 shows a longitudinal section through an unlocking device usable for the holding arm according to FIG. 1 according to the first embodiment in a state in which a handle of the unlocking device is not operated and the holding arm is locked.

FIG. 2 shows an unlocking device 50 in a longitudinal section as first embodiment. The unlocking device 50 is suited to unlock the holding arm 10 shown in FIG. 1 in the manner described below.

The unlocking device 50 may have an elongated housing 52 which is formed from two housing parts 54 and 56 being coupled together via screwed connections 58 and 60. The unlocking device 50 may further include a handle 62 being manually operable by an operator, a conversion mechanism generally referred to with 64 in FIG. 2 and a trigger rod 66 movably guided along the housing longitudinal axis. The conversion mechanism 64 may be formed by a transmission in the first embodiment which comprises a toothed wheel portion 68 formed at the handle 62 and a toothed rack 70 meshed with the toothed wheel portion 68. The toothed rack 70 may be part of a force transfer element 72 which includes a hollow cylindrical portion 74 at the end thereof facing away from the toothed rack 70.

At the end of the trigger rod 66 facing the handle 62 a support 76 may be installed which together with a rigid, hollow cylindrical end stop 78 defines a space in which a pressure loadable coil spring 80 is arranged.

The trigger rod 66 may extend through a through bore 82 formed in the housing part 56. Thereby, the trigger rod 66 may be movably guided in the direction of the longitudinal axis of the housing 52. The trigger rod 66 may serve to operate an unlocking mechanism which is included in the holding arm not shown in FIG. 2. Of this unlocking mechanism in FIG. 2 only a single unlocking component 84 is illustrated which is pivotably supported about a pivoting axis 86. Due to the trigger rod 66 pressing onto the unlocking component 84 the latter is moved about the pivoting axis 86 for unlocking the holding arm.

The coil spring 80 via which the force transfer element 72 is coupled to the trigger rod 66 may form a force limiter which provides for the operating force being manually exerted by the operator on the handle 62 being (e.g., only) transferred via the conversion mechanism 65 to the trigger rod 66 and thus to the unlocking component 84, if the operating force does not exceed a predetermined force.

The spring force with which the coil spring 80 counteracts its compression is selected (e.g., exactly selected) such that the coil spring 80 is only compressed, if the operating force exceeds the predetermined force. In this case, the coil spring 80 (e.g., quasi) absorbs the operating force exerted via the handle 62 on the force transfer element 72 by being elastically compressed. If the operating force is, however, smaller or equal to the predetermined force, it may not be sufficient to compress the coil screw 80. The coil spring 80 then forms a rigid coupling element between the force transfer element 72 and the trigger rod 66, so that the movement of the force transfer element 72 caused by operating the handle 62 is converted into a corresponding movement of the trigger rod 66 in the direction of the longitudinal axis of the housing 52 causing the unlocking component 84 to be moved about the pivoting axis 86 and ultimately the holding arm to be unlocked.

Figure 3:
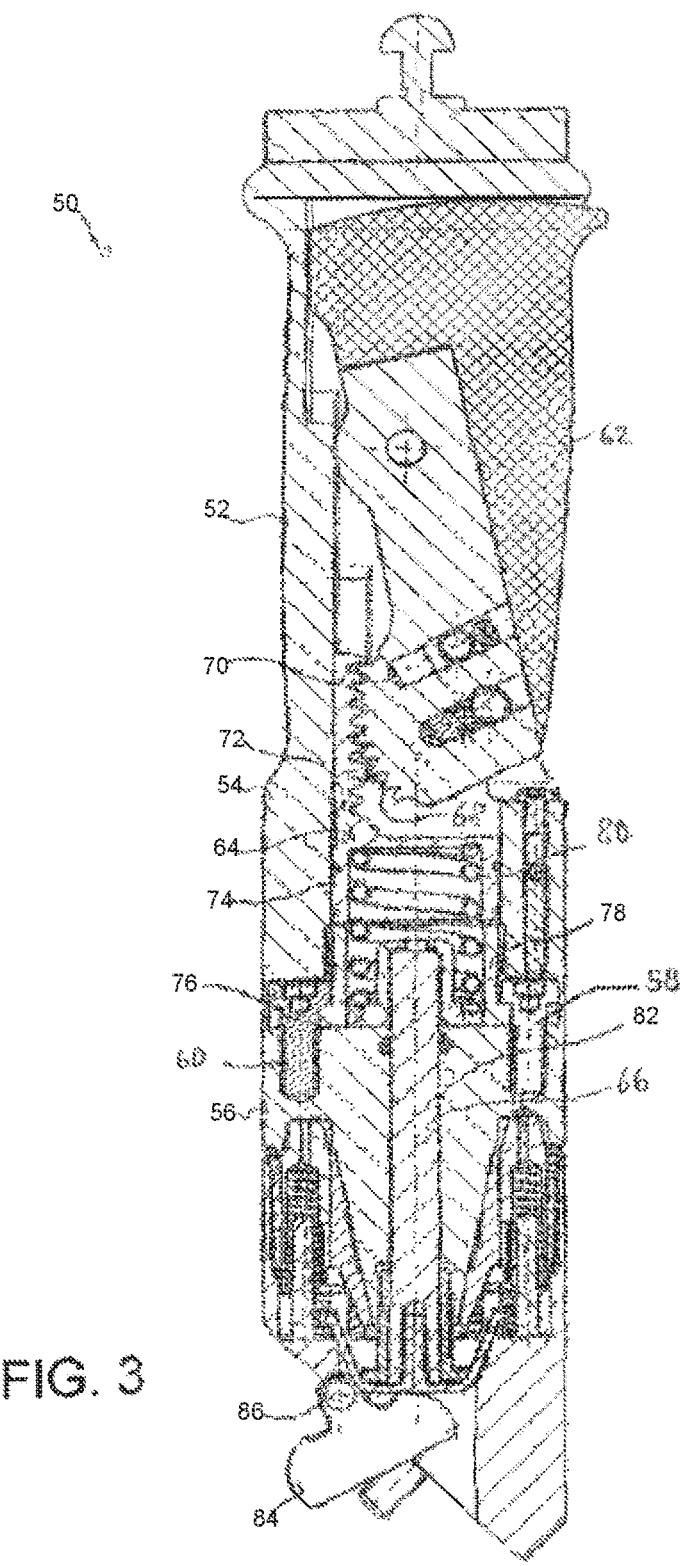
FIG. 3 shows a longitudinal section through the unlocking device according to FIG. 2 in a state in which the handle is operated and as a result the holding arm is unlocked.
Figure 4:
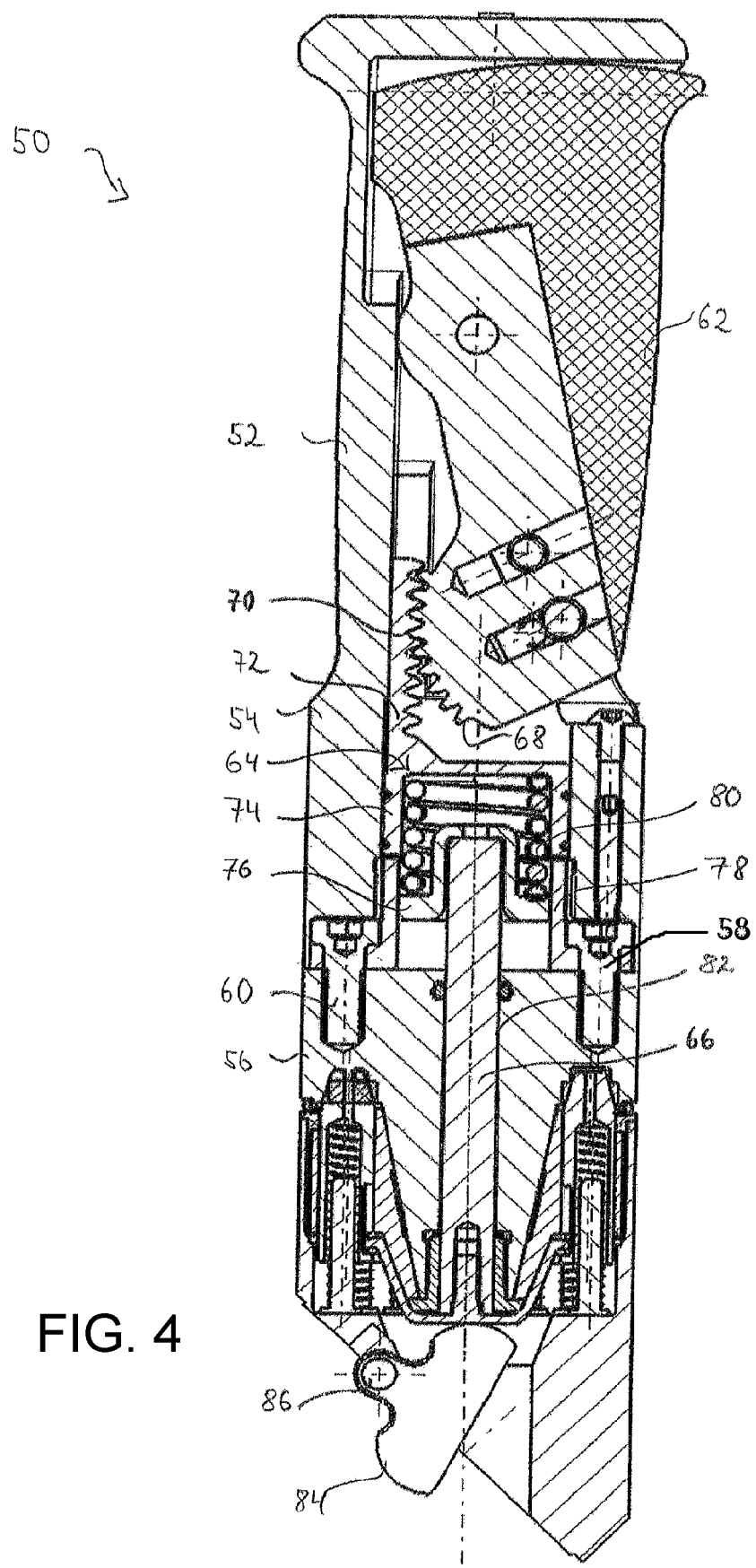
FIG. 4 shows a longitudinal section through the unlocking device according to FIG. 2 in a state in which the handle is operated and the holding arm still remains locked.

FIGS. 2 to 4 illustrate the mode of operation of the unlocking device 50, for example of the force limiter formed by the coil spring 80.

In FIG. 2, the handle 62 is for example not operated. Correspondingly the trigger rod 66 remains in its locking position in which it does not act on the unlocking component 84. The holding arm is locked.

In FIG. 3, the handle 62 may be operated with a (load dependent) operating force, which may not be sufficient to compress the coil screw 80 significantly. Thus, in this state the coil screw 80 forms a substantially rigid element which is moved together with the force transfer element 72 in the direction of the longitudinal axis of the housing 52 downwards until the hollow cylindrical portion 74 of the force transfer element 72 abuts the rigid end stop 78. Thus, the operating force may be transferred to the trigger rod 66 causing it to be moved in its unlocking position and the unlocking component 84 to be pivoted about the pivoting axis 86. The holding arm may be unlocked.

In FIG. 4, the handle 62 may be operated with a (load dependent) operating force, which may be large enough to compress the coil spring 80. The coil spring 80 thus absorbs the exerted operating force causing the trigger rod 62 to remain in its locking position and not to act on the unlocking component 84. The holding arm 62 remains locked despite of the operation of the handle 62.

Figure 5:
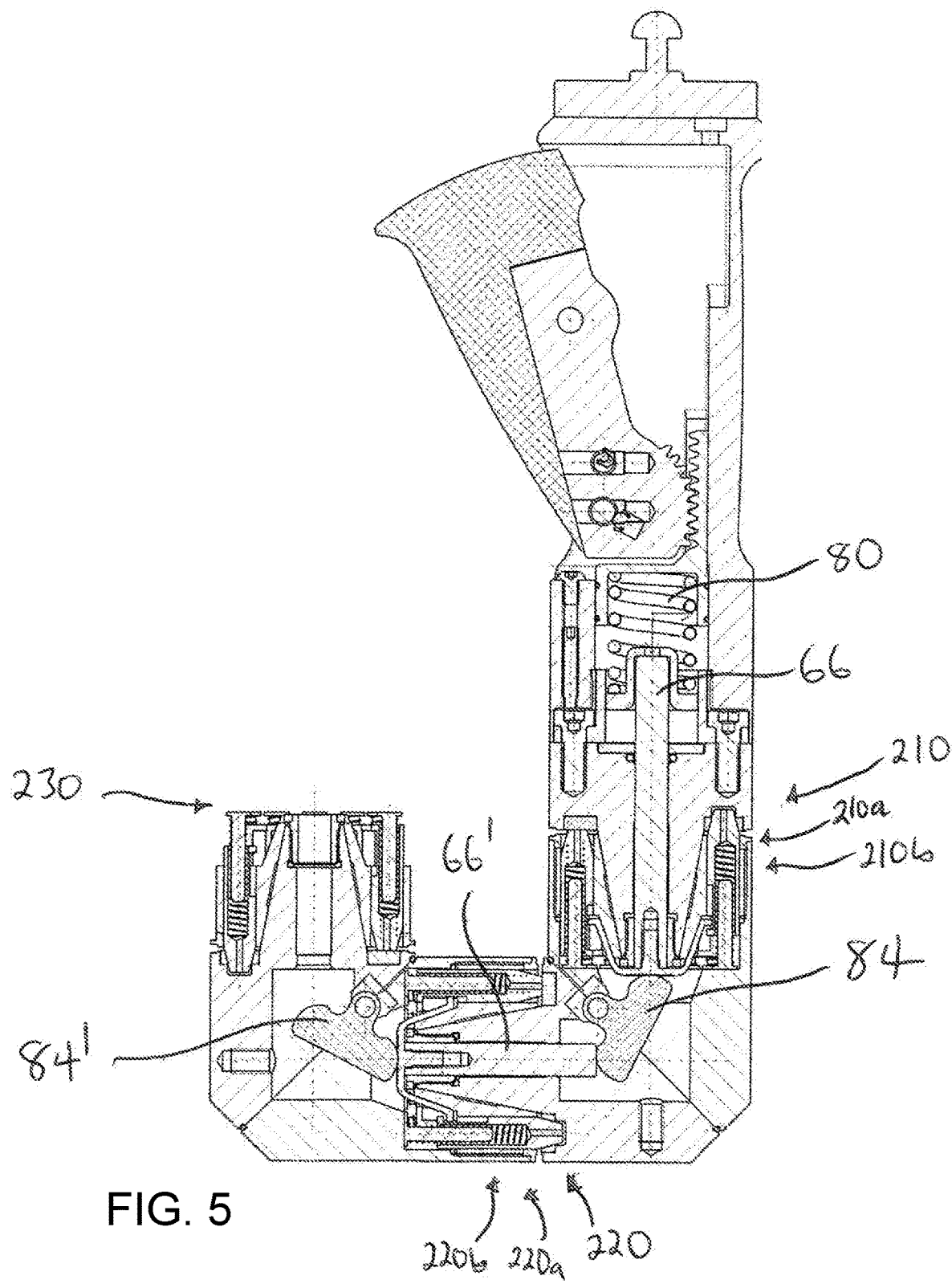
FIG. 5 shows a longitudinal section through the unlocking device according to FIG. 2 in a state in which the handle is not operated and the holding arm remains locked.
Figure 6:
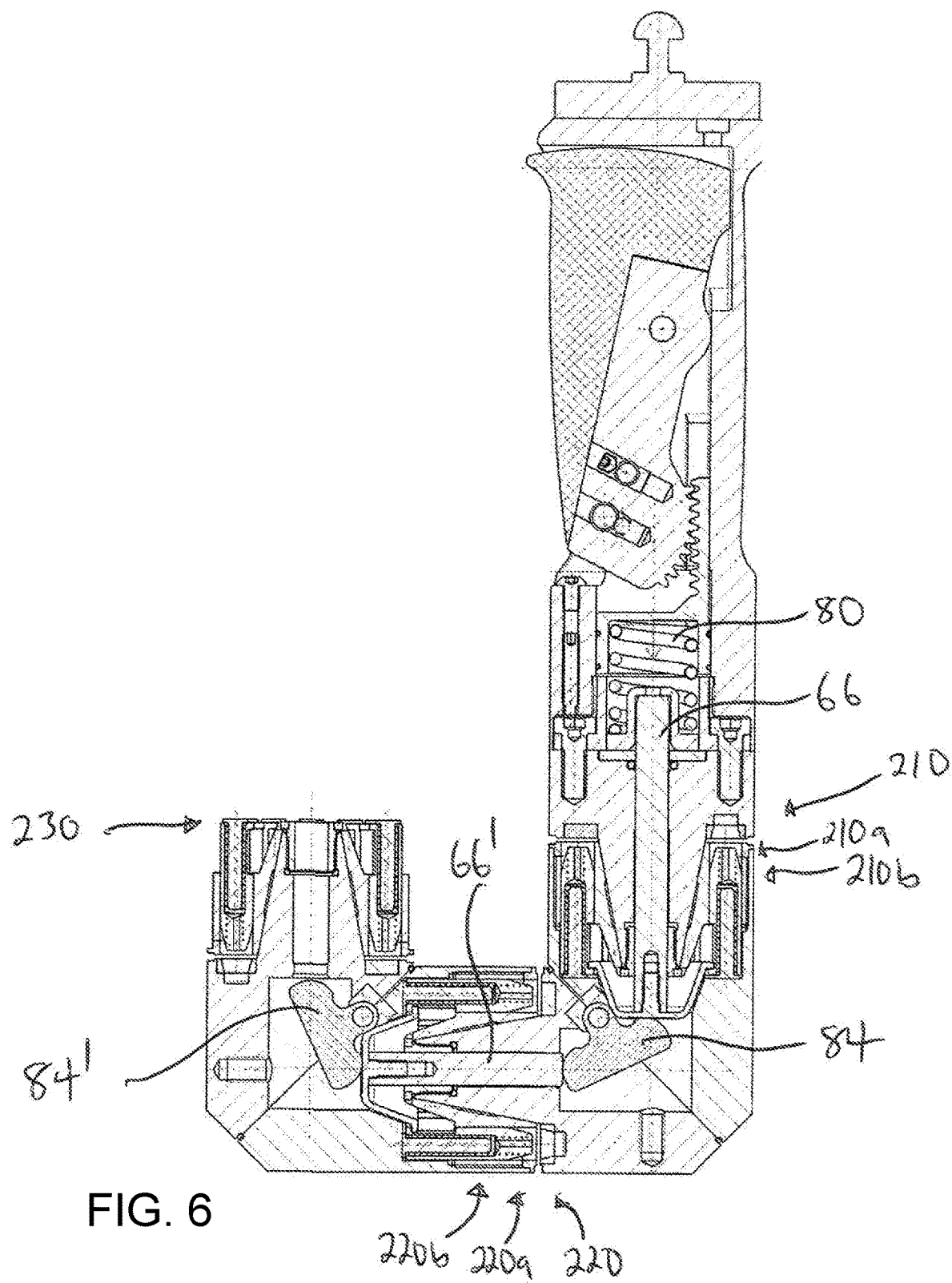
FIG. 6 shows a longitudinal section through the unlocking device according to FIG. 2 in a state in which the handle is operated and the holding arm is unlocked.
Figure 7:
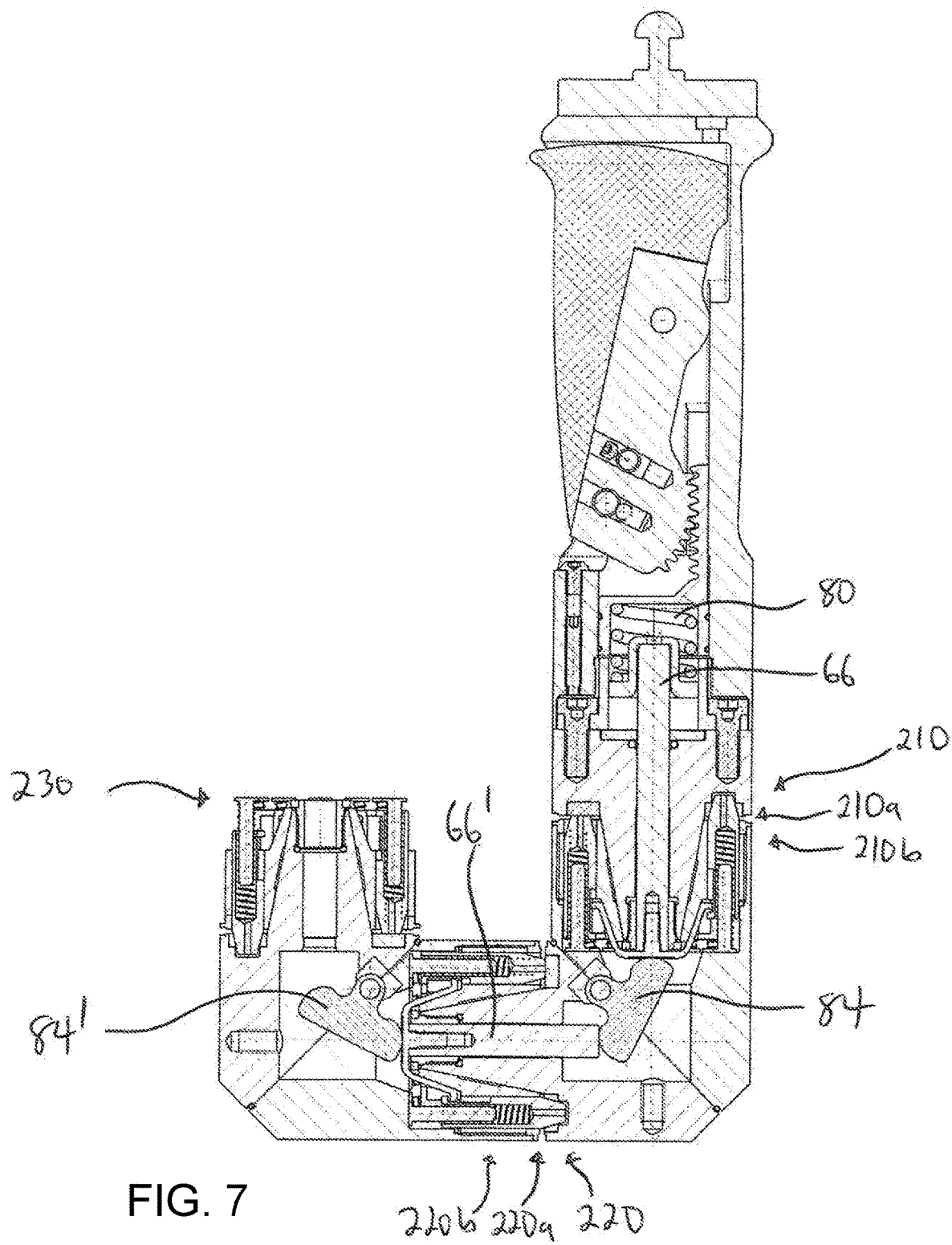
FIG. 7 shows a longitudinal section through the unlocking device according to FIG. 2 in a state in which the handle is operated and the holding arm remains locked.

FIGS. 5 through 7 illustrate how arm 10 and unlocking device 50 may operate together. In at least some exemplary embodiments, the force applied by a user via handle 62 and for example a toothed rack may be converted into a longitudinal displacement of trigger rod 66. Trigger rod 66 may be urged (e.g., shoved or pushed) in holding arm 10 along an axis of holding member 12 via pressing or pushing of handle 62. Trigger rod 66 may be included with each of the holding members 12, 14, 16, 18, 20, and 22 (e.g., trigger rod 66'). The movement of the trigger rod 66 may be passed (e.g., passed on) from holding member to holding member 12, 14, 16, 18, 20, and 22, via the unlocking component 84 (and, e.g., 84'), until the last holding member 22. The holding members 12, 14, 16, 18, 20, and 22 may be connected to each other in interfaces or fittings 24, 26, 28, 30, and 32 via respective screws (e.g., 210b and 220b, as illustrated in FIGS. 5-7). In each fitting 24, 26, 28, 30, and 32, an unlocking component 84 may pass on (e.g. forward) movement and force on to the next trigger rod (e.g., 66' and so on). Trigger rod 66 (e.g., and 66' and so on) may be actuated in arm 10 along the axes of the holding members 12, 14, 16, 18, 20, and 22 by the pressing (e.g., pushing) of handle 62, as illustrated for example in FIG. 6. In this manner, some or all of the rotational joints 210, 220, 230, 240, 250, and 260 may be released. Arm 10 may now be freely movable (e.g., infinitely variably positionable) over the released joints.

By a user or operator letting go of handle 62, handle 62 as well as the trigger rod 66 and/or 66') may be put back returned) to their starting position (e.g., by spring force) With the rotational joints 210, 220, 230, 240, 250, and 260 now blocked, the arm 10 remains substantially rigid in its set position. Coil screw 80 may be switched (e.g., connected) between the release mechanism and trigger rod 66. The coil screw 80 may operate so that even by the loading of the arm 10, the user can press handle 62, and nevertheless the trigger rod 66 may not be actuated or moved (e.g., not activated). By loading of the arm 10, the joint locks (e.g., 210a and 220a) may be braced. The hand force to be applied to move or actuate handle 62 may rise with the increase of the load on the arm 10 (e.g., by the patient). At that point, for example, if the release force exceeds the spring force of the coil screw 80, then the movement of the handle 62 will not be transferred to the trigger rod (e.g., 66 or 66'), but instead may be absorbed in the travel (e.g., displacement) of the coil screw 80 as illustrated in FIG. 7.

Figure 8:
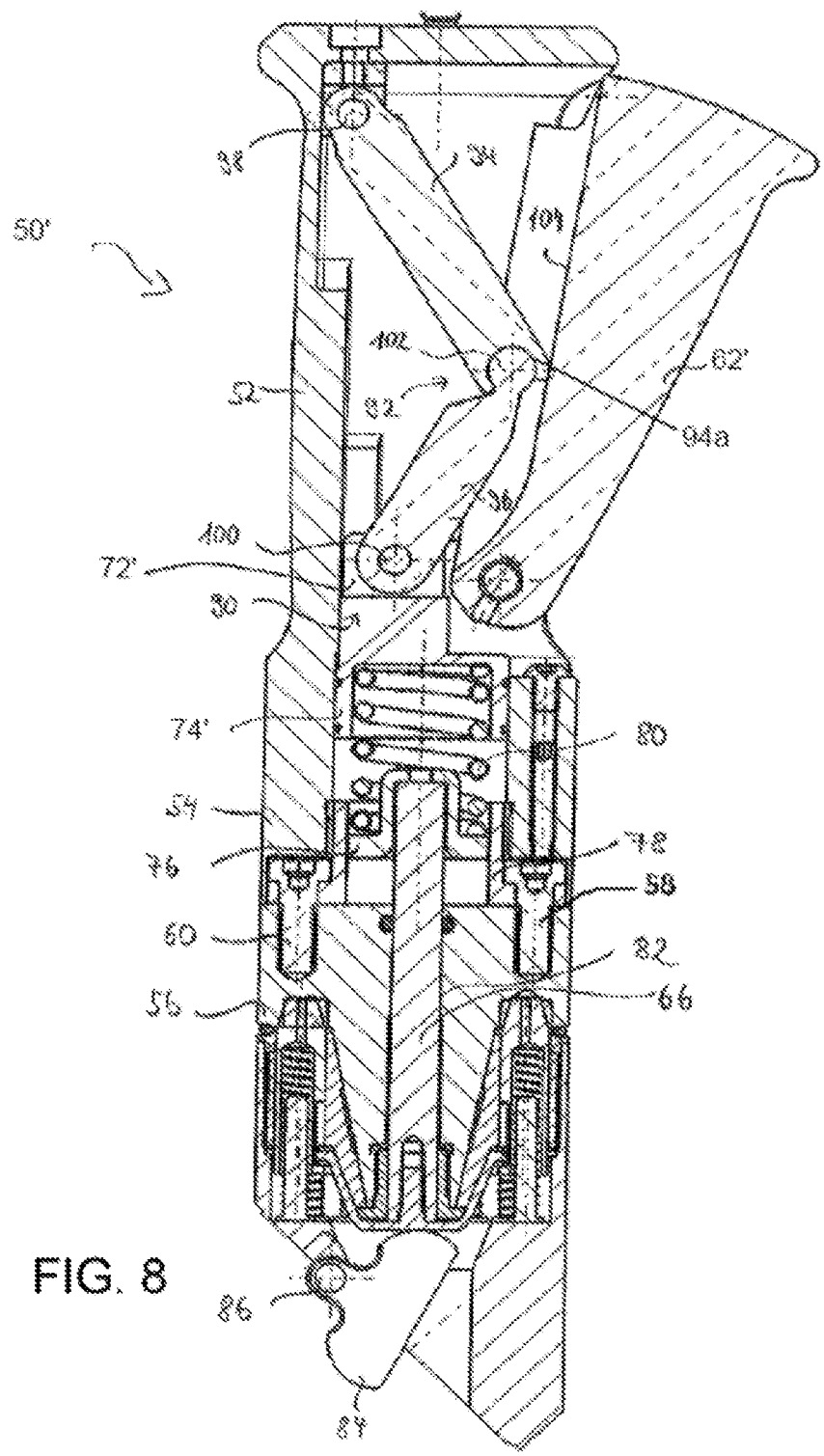
FIG. 8 shows a longitudinal section through a locking device usable for the holding arm according to FIG. 1 according to the second embodiment in a state in which the handle of the locking device is not operated and the holding arm is locked.
Figure 9:
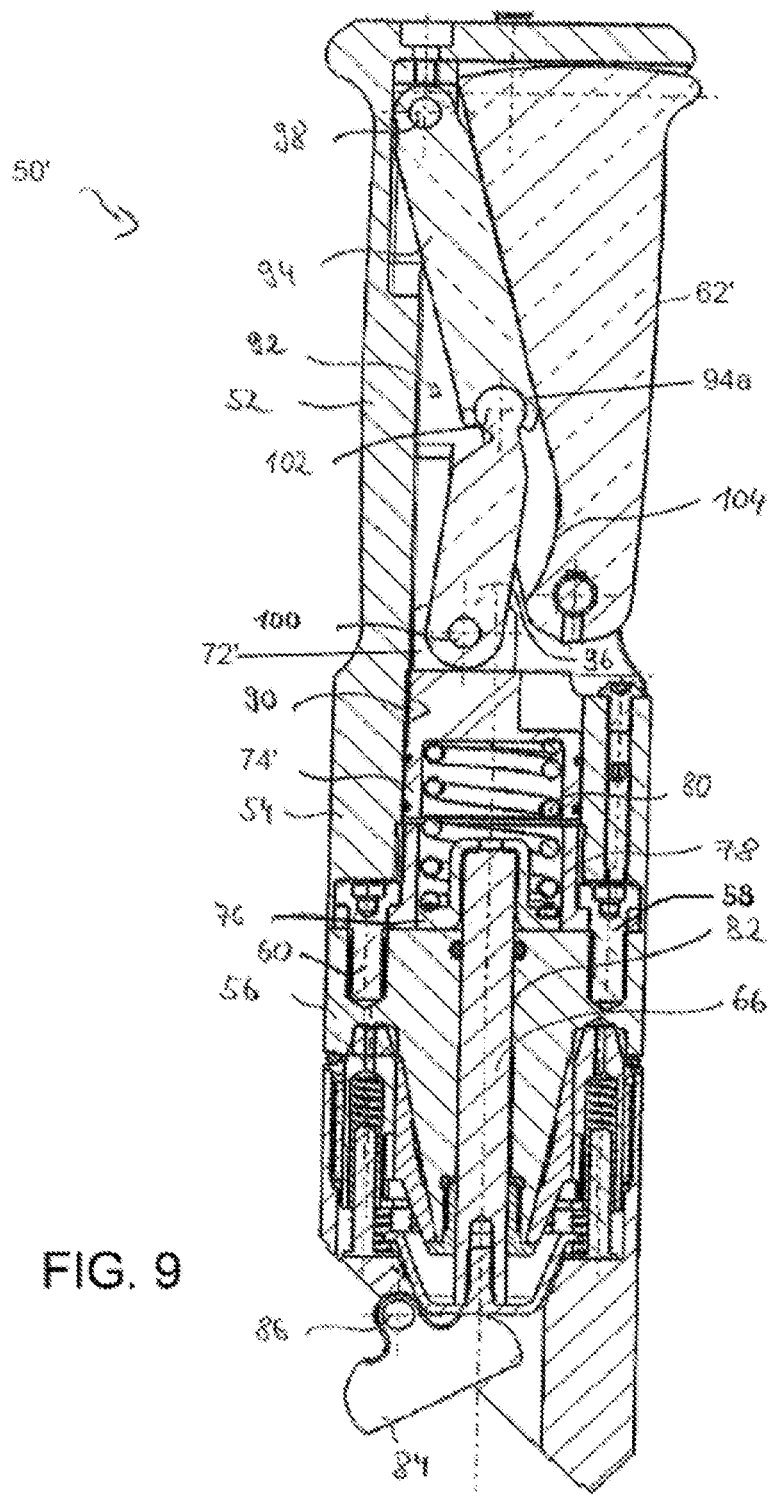
FIG. 9 shows a longitudinal section through the unlocking device according to FIG. 8 in a state in which the handle is operated and the holding arm is unlocked.
Figure 10:
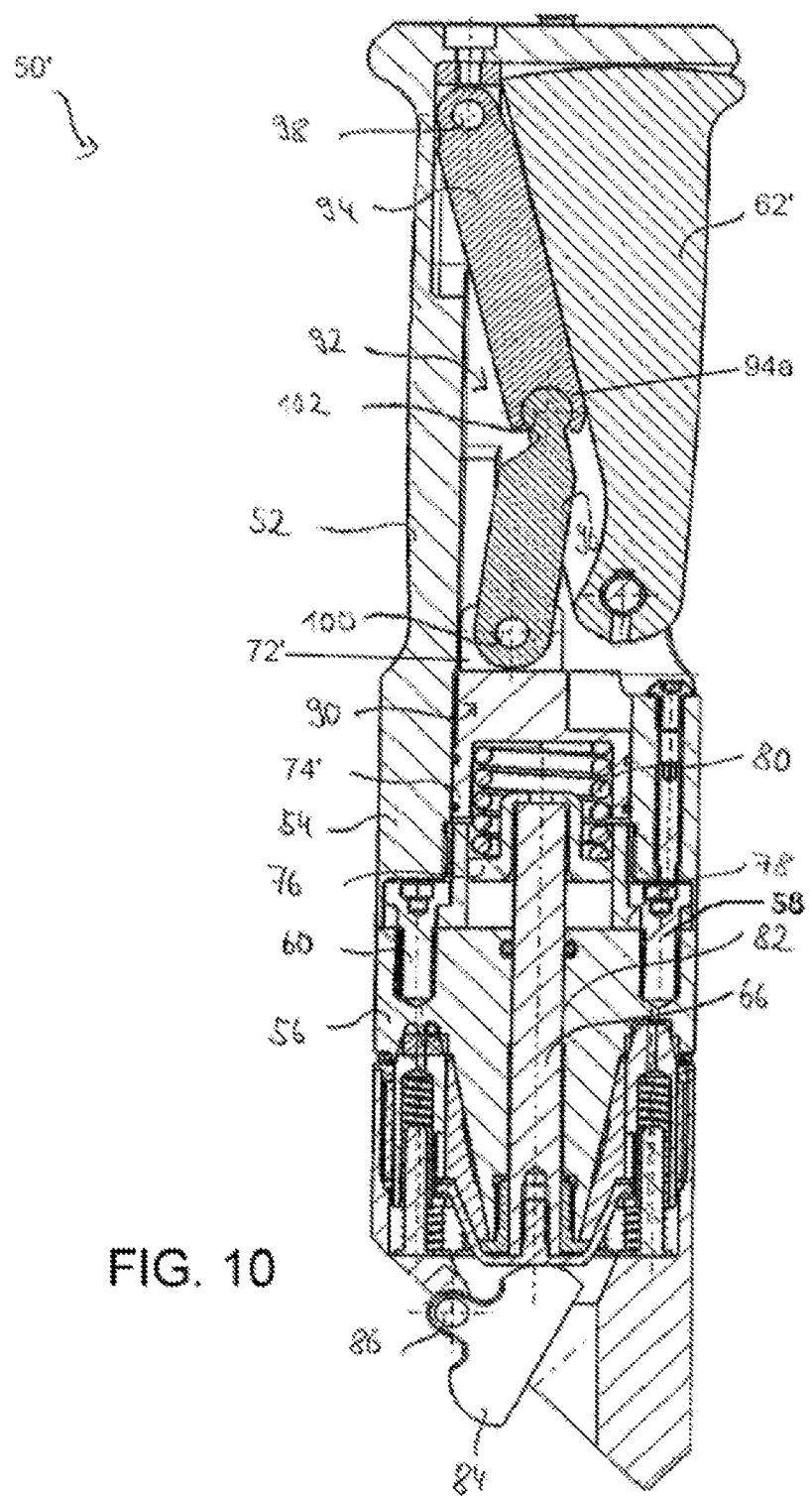
FIG. 10 shows a longitudinal section through the unlocking device according to FIG. 8 in a state in which the handle is operated and the holding arm still remains locked.

In FIGS. 8 to 10, a modification of the unlocking device 501 is illustrated as a second embodiment. The second embodiment differs from the first embodiment shown in FIGS. 2 to 4 by for example a modified conversion mechanism, which is referred to with reference numeral 90 in FIGS. 8 to 10. Said components of the second embodiment which may correspond in their function with those of the first embodiment are provided with the reference signs used in the first embodiment.

The conversion mechanism 90 modified with respect to the first embodiment includes a toggle lever 92, which may be formed from a longer first leg 94 and a shorter second leg 96. The first leg 94 is supported with one end at a pivot axis 98 which may be rigidly installed in the housing 52. The pivoting axis 98 may thus form a first center of rotation of the toggle lever 92 stationary relative to the housing 52. The second leg 96 may be supported with its end facing away from the first leg 94 at a pivoting axis 100, which may be rigidly installed at the force transfer element 72', which may be movable in the direction of the longitudinal axis of the housing 52. The pivoting axis 100 may thus form a second center of rotation which is moved together with the force transfer element 72'. The force transfer element 72' of this embodiment may include a hollow cylindrical portion 74' as shown in FIG. 8.

At the ends thereof facing each other, the two legs 94 and 96 may be rotatably coupled to each other. For this, the second leg 96 may include an approximately spherical portion 102, which may be supported in a corresponding spherical receptacle, which is formed at the end of the first leg 94a facing the second leg. By this rotatable coupling of the two legs 94 and 96 a common movable third center of rotation of the toggle lever 92 may be provided.

The toggle lever 92 abuts in the region of its third center of rotation a pressing surface 104 formed at the handle 62'. If the operator operates the handle 62', the two legs 94 and 96 may be, as shown in FIG. 9, aligned vertically bringing the toggle lever 92 altogether in a form in which it is positioned approximately parallel to the longitudinal axis of the housing 92. By this alignment of the toggle lever 92 the operating force exerted on the handle 62' may be transferred to the force transfer element 72', causing it to be moved downwards in the direction of the longitudinal axis of the housing 52 (for example as shown in FIGS. 8 to 10).

The second embodiment shown in FIGS. 8 to 10 may operate in a similar manner as the first embodiment according to FIGS. 2 to 4. For that matter, the state shown in FIG. 8 in which the handle 62' is not operated and the holding arm is consequently locked may correspond to the state according to FIG. 2, while the state illustrated in FIG. 9 in which the handle 62' is operated and the holding arm is unlocked corresponds to the state according to FIG. 3 and the state shown in FIG. 10 in which the handle 62' is operated, but the holding arm remains locked may correspond to the state according to FIG. 4.

Figure 11:
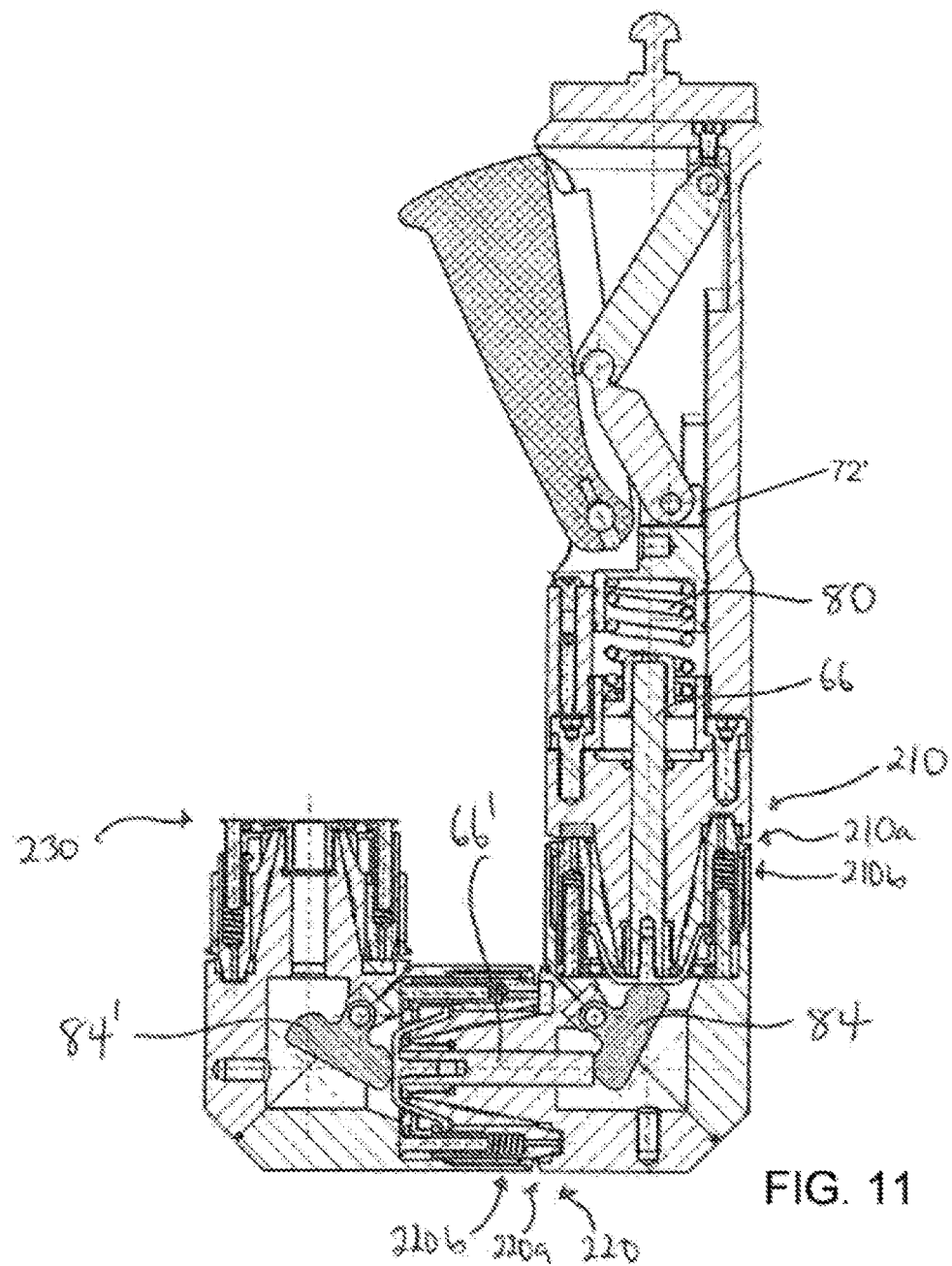
FIG. 11 shows a longitudinal section through the unlocking device according to FIG. 8 in a state in which the handle is not operated and the holding arm remains locked.
Figure 12:
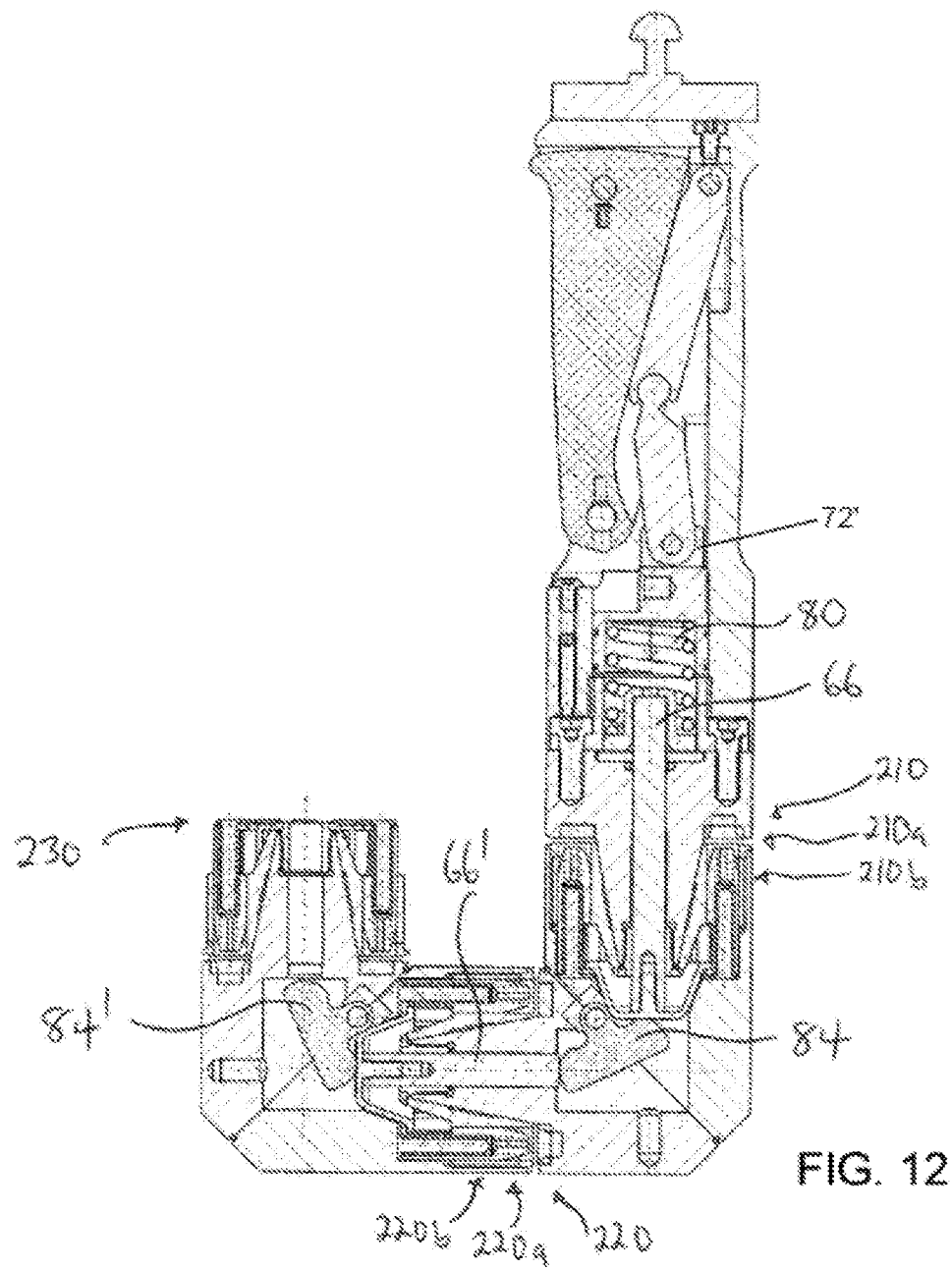
FIG. 12 shows a longitudinal section through the unlocking device according to FIG. 8 in a state in which the handle is operated and the holding arm is unlocked.
Figure 13:
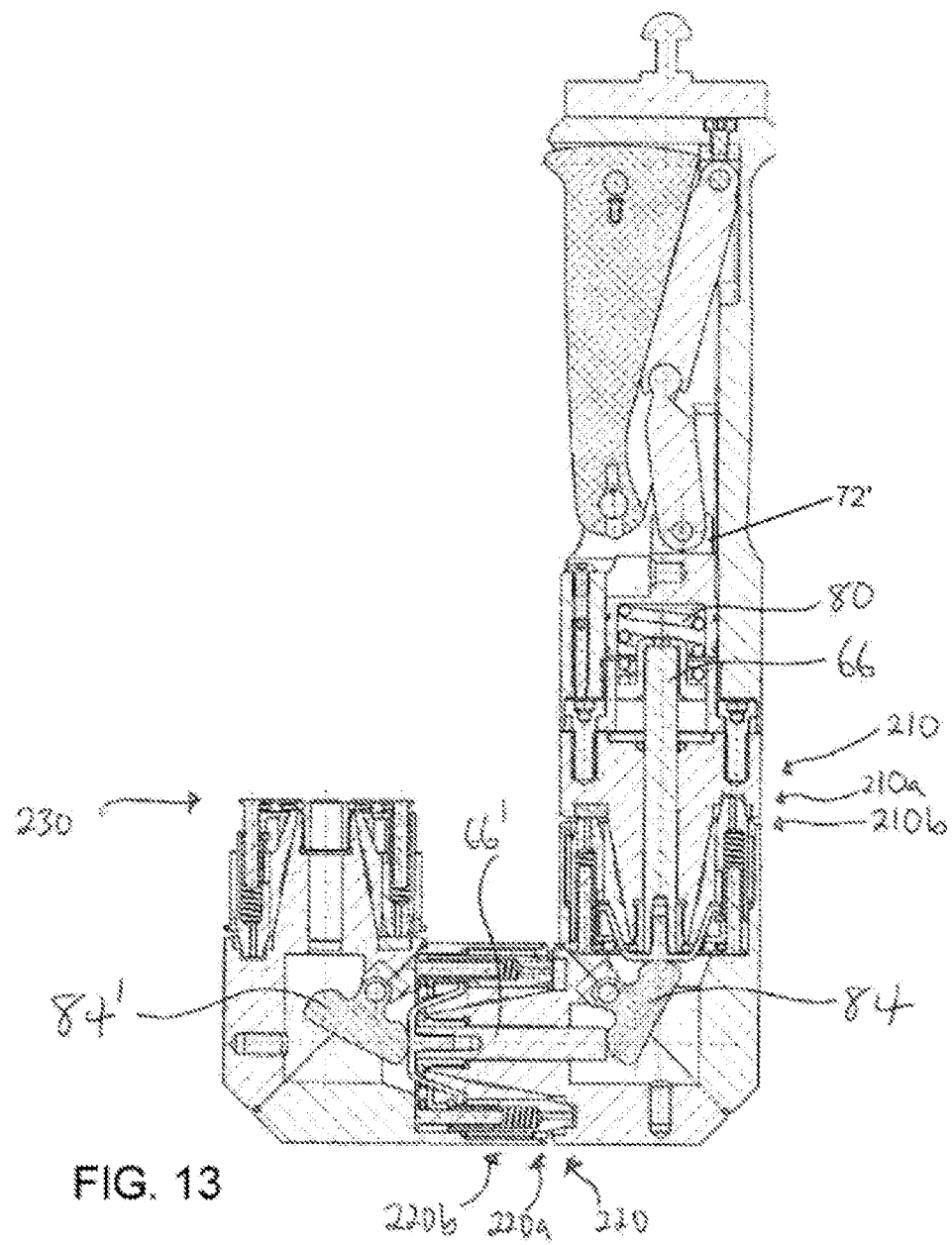
FIG. 13 shows a longitudinal section through the unlocking device according to FIG. 8 in a state in which the handle is operated and the holding arm remains locked.

The exemplary embodiment as shown in FIGS. 11-13 may operate similarly as described above for the exemplary embodiment shown in FIGS. 5-7.

Based on the above exemplary embodiments, for example, an operator of arm 10 may unload the arm 10 prior to suitable release of the joints of the arm. Accordingly for example, the operator may thereby be prepared for the application of load (e.g., weight of a patient) and may therefore not be surprised that a large load is being carried by arm 10 during operation.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. An unlocking device for unlocking a holding arm, the unlocking device comprising:
   a housing;
   an operating element which is manually movable by an operator for unlocking the holding arm via an operating force;
   a conversion mechanism which includes a force transfer element operatively coupled to the operating element for movement by the operating element,
   a trigger comprising a first end and a second end, the first end of the trigger being coupled to the force transfer element, the trigger being longitudinally movable within the housing in response to movement of the operating element which is transferred to the trigger by the conversion mechanism; and
   an unlocking component in contact with the second end of the trigger, the unlocking component being configured to pivot in response to longitudinal movement of the trigger;
   wherein the unlocking component is pivotally mounted on a surface of the housing such that when the operating element is actuated, the trigger is longitudinally movable within the housing and the second end of the trigger presses the unlocking component causing the unlocking component to pivot outwardly from the housing, wherein the conversion mechanism includes an elastically deformable force limiter via which the force transfer element is coupled to the trigger, and wherein a compressing force of the elastically deformable force limiter limits the operating force which is transferable from the operating element to the trigger.

2. The unlocking device according to claim 1, wherein the conversion mechanism converts the operating force manually exerted on the operating element into a movement of the force transfer element along a housing longitudinal axis, and the elastically deformable force limiter is elastically deformable along the housing longitudinal axis.

3. The unlocking device according to claim 1, wherein the elastically deformable force limiter is a spring.

4. The unlocking device according to claim 1, wherein the operating element includes a first toothing and the force transfer element includes a second toothing, the second toothing being meshed with the first toothing.

5. The unlocking device according to claim 1:
wherein the conversion mechanism further comprises a toggle lever having a first leg and a second leg,
wherein the operating element includes a pressing surface;
wherein the first leg of the toggle lever is rotatably supported at a first end in a first center of rotation inside the housing,
wherein the second leg of the toggle lever is rotatably supported at a first end in a second center of rotation,
wherein the first leg and the second leg are rotatably supported respectively at a second end in a common third center of rotation, and
wherein the pressing surface during manual operation of the operating element presses onto the toggle lever at the third center of rotation.

6. The unlocking device according to claim 1, wherein the operating element is a pivotably supported handle.

7. The unlocking device according to claim 1, wherein the force transfer element includes a hollow cylindrical portion in which the force limiter is supported.

8. The unlocking device according to claim 1, wherein the trigger includes a trigger rod.

9. The unlocking device according to claim 1:
wherein the conversion mechanism further comprises a toggle lever having a first leg and a second leg;
wherein the operating element includes a handle and a pressing surface;
wherein the first leg and the second leg are movably connected, and
wherein during manual operation of the operating element, the pressing surface presses onto the toggle lever to cause partial straightening of the toggle lever, to thereby force a bottom end of the second leg towards the force transfer element to thereby exert axial pressure on the trigger rod.

10. The unlocking device according to claim 1, wherein the operating element comprises a handle, the handle being manually compressible into the housing of the unlocking device.

11. The unlocking device according to claim 1, further comprising an end stop, the end stop positioned for limiting elastic deformation of the force limiter;
wherein the end stop is formed by an end stop surface that abuts the force transfer element.

12. The unlocking device according to claim 1:
wherein movement of the operating element, when the operating element is moved manually by an operator for unlocking the holding arm via the operating force, is in an inward direction toward the housing.

13. An unlocking device for unlocking a holding arm, the unlocking device comprising:
a housing;
an operating element which can be operated manually for unlocking the holding arm via an operating force,
a conversion mechanism which includes a force transfer element operatively coupled to the operating element for movement by the operating element,
a trigger coupled to the force transfer element and moveable with respect to the a housing, wherein the trigger is movable by the operating force transferred by the force transfer element to the trigger from (i) a locked position in which the trigger does not displace an unlocking component, to (ii) an unlocked position in which the trigger presses the unlocking component and holds the unlocking component in a displaced position,
wherein the conversion mechanism includes an elastically deformable force limiter via which the force transfer element is operatively coupled to the trigger and which limits, due to the elastic deformation thereof, a transfer of the operating force from the operating element to the trigger, if the operating force exceeds a predetermined force, and
an end stop, the end stop positioned for limiting elastic deformation of the force limiter,
wherein the end stop is formed by an end stop surface that abuts the force transfer element.

14. The unlocking device according to claim 13, wherein the conversion mechanism converts the operating force manually exerted on the operating element into a movement of the force transfer element and the trigger along a housing longitudinal axis, and the force limiter is elastically deformable along the housing longitudinal axis;
wherein the operating element comprises a handle which is pivotally movable into the housing by the operating force; and
wherein the handle pivots relative to the housing longitudinal axis.

15. An unlocking device for unlocking a holding arm, the unlocking device comprising:
a housing,
a handle which is manually movable for unlocking the holding arm, the handle comprising a pressing surface,
a force transfer element operatively coupled to the handle,
a trigger coupled to the force transfer element,
an elastically deformable force limiter via which the force transfer element is coupled to the trigger, and
a conversion mechanism, the conversion mechanism comprising the force transfer element and a toggle lever having a first leg and a second leg,
wherein the first leg of the toggle lever is rotatably supported at a first end in a first center of rotation inside the housing,
wherein the second leg of the toggle lever is rotatably supported at a first end in a second center of rotation,
wherein the first leg and the second leg are rotatably supported at respective second ends at a common third center of rotation,
wherein during manual operation of the handle the pressing surface presses onto the toggle lever in a region of the third center of rotation to actuate the force transfer element, and wherein the trigger is movable by an operating force transferred by the force transfer element to the trigger from (i) a locked position in which the trigger does not displace an unlocking component from within the housing into (ii) an unlocked position in which the trigger presses and displaces the unlocking component by pivoting the unlocking component outwardly from within the housing.

16. The unlocking device according to claim 15:

wherein the first leg and the second leg are inside the housing; and wherein the handle is compressible into the housing to actuate the force transfer element.

17. The unlocking device according to claim 15, wherein the elastically deformable force limiter is a spring.

18. The unlocking device according to claim 15:

wherein the housing has a housing axis;

wherein the force transfer element and the toggle lever are within the housing;

wherein during manual operation of the handle said pressing of the pressing surface onto the toggle lever in a region of the third center of rotation moves the third center of rotation towards the housing axis, and moves the trigger along the housing axis.

19. The unlocking device according to claim 15:

wherein the first center of rotation is inside the housing; and wherein a holder is positioned on the housing, the holder being configured for connection with a load for supporting the load when present.

\* \* \* \* \*